US00PP11152P

United States Patent [19]

Glicenstein

[11] Patent Number: Plant 11,152

[45] Date of Patent: Dec. 14, 1999

[54] AZALEA PLANT NAMED 'PARASOL'

[75] Inventor: Leon Glicenstein, State College, Pa.

[73] Assignee: Yoder Brothers, Inc., Barberton, Ohio

[21] Appl. No.: 09/082,073

[22] Filed: May 20, 1998

[51] Int. Cl.[6] ..... A01H 5/00

[52] U.S. Cl. ..... Plt./238

[58] Field of Search ..... Plt./238, 239, 240

[56] References Cited

U.S. PATENT DOCUMENTS

P.P. 2,770 10/1967 Kerrigan ..... Plt./238

P.P. 7,530 5/1991 Mossholder ..... Plt./240

*Primary Examiner*—Howard J. Locker

*Assistant Examiner*—Kent L. Bell

*Attorney, Agent, or Firm*—C. A. Whealy

[57] ABSTRACT

A new and distinct cultivar of Azalea plant named 'Parasol', characterized by its large and vigorous plants that are freely branching; shiny, dark green, and broad leaves; very freely flowering; large, showy, ruffled, single flowers; long-lasting light pink to white and hot pink bi-colored flowers that resist fading; excellent postproduction longevity with plants maintaining good flower substance for about four weeks in an interior environment; and good resistance to Cylindrocladium.

1 Drawing Sheet

BACKGROUND OF THE INVENTION

The present invention relates to a new and distinct cultivar of Azalea, botanically known as *Rhododendron hybrida,* an evergreen greenhouse-forcing type, and hereinafter referred to by the name 'Parasol'.

The new Azalea is a product of a planned breeding program conducted by the inventor in Alva, Fla. The objective of the breeding program is to create new Azalea varieties having uniform plant habit and uniform flowering, numerous flowers, good foliage retention during the cooling and forcing periods, and excellent postproduction longevity.

The new Azalea originated from a cross made by the inventor in Alva, Fla., of the commercial cultivar *Rhododendron hybrida* 'Fascination' (not patented) as the female, or seed, parent with the commercial cultivar *Rhododendron hybrida* 'Prize' (disclosed in U.S. Plant Pat. No. 3,795) as the male, or pollen, parent.

Compared to plants of the red-edged female parent, 'Fascination', plants of the new Azalea have a more uniform plant habit and less pink in the center of the flower.

In addition to flower color and form, plants of the new Azalea have larger flowers and flower slower and not as uniformly as plants of the dark rose double hose-in-hose-flowered 'Prize'.

Compared to plants of the new Azalea's sibling cultivar, 'Tapestry', disclosed in U.S. Plant Pat. application Ser. No. 09/082,053, flowers of plants of the new Azalea are light pink to white and hot pink bi-colored whereas flowers of plants of the cultivar 'Tapestry' are light pink to white and red bi-colored. In addition, plants of the new Azalea are more floriferous, but have smaller flowers than plants of the cultivar 'Tapestry'.

The new Azalea was discovered and selected by the inventor as a flowering plant within the progeny of the stated cross in a controlled environment in Alva, Fla., on May 24, 1994. The selection of this plant was based on its desirable flower color, profuse and uniform flowering, uniform plant habit, excellent foliage retention, resistance to Cylindrocladium and good postproduction longevity.

Asexual reproduction of the new Azalea by terminal cuttings taken in a controlled environment in Alv, Fla., has shown that the unique features of this new Azalea are stable and reproduced true to type in successive generations.

The new Azalea has not been observed under all possible environmental conditions. The phenotype may vary somewhat with variations in environment such as temperature, daylength, light intensity, nutrition and water status without, however, any variance in genotype.

BRIEF SUMMARY OF THE INVENTION

The following traits have been repeatedly observed and are determined to be in the unique characteristics of 'Parasol'. These characteristics in combination distinguish 'Parasol' as a new and distinct cultivar:

1. Large and vigorous plants that are freely branching.
2. Shiny, dark green, and broad leaves.
3. Very freely flowering.
4. Large, showy, ruffled, single flowers.
5. Long-lasting light pink to white and hot pink bi-colored flowers that resist fading.
6. Excellent postproduction longevity with plants maintaining good flower substance for about four weeks in an interior environment.
7. Good resistance to Cylindrocladium.

Plants of the new Azalea can be compared to plants of the red-edged flowered cultivar 'Leopold Astrid' (not patented). However, in side-by-side comparisons conducted in Alva, Fla., plants of the new Azalea differ from plants of the cultivar 'Leopold Astrid' in the following characteristics:

1. Plants of the new Azalea are more vigorous, upright and stronger than plants of the cultivar 'Leopold Astrid'.
2. Flowers of plants of the new Azalea are single whereas flowers of plants of the cultivar 'Leopold Astrid' are double in form.
3. Plants of the new Azalea are more resistant to Cylindrocladium.

BRIEF DESCRIPTION OF THE PHOTOGRAPHS

The accompanying colored photographs illustrate the overall appearance of the new Azalea, showing the colors as true as it is reasonably possible to obtain in colored reproductions of this type.

The photograph at the top of the sheet comprises a side perspective view of a typical plant of 'Parasol'.

The photograph at the bottom of the sheet is a close-up view of typical flowers of 'Parasol'. Flower and foliage colors in the photographs may appear different from the actual colors due to light reflectance.

DETAILED BOTANICAL DESCRIPTION

The aforementioned and following observations, measurements, values, and comparisons describe plants grown in Alva, Fla., in 12.5-cm containers with day temperatures ranging from 16 to 35° C. and night temperatures ranging from 10 to 24° C. Plants were grown under 50 percent polypropylene shade cloth reducing ambient light levels to about 4,000 to 5,000 footcandles. After flower bud development, plants were cooled at 3 to 5° C. for six weeks to break flower bud dormancy. Plants were subsequently forced into flower under commercial conditions in a polyethylene-covered greenhouse.

In the following description, color references are made to The Royal Horticultural Society Colour Chart except where general terms of ordinary dictionary significance are used.

Botanical classification:

*Botanical.*—*Rhododenron hybrida* 'Parasol'.

*Commercial.*—Evergreen greenhouse-forcing type Azalea.

Parentage:

*Male or pollen parent.*—*Rhododendron hybrida* 'Prize', U.S. Plant Pat. No. 3,795.

*Female or seed parent.*—*Rhododendron hybrida* 'Fascination', not patented.

Propagation:

*Type.*—By terminal cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Rooting habit.*—Vigorous and finely-branched.

Plant description:

*Plant form and growth habit.*—Perennial, evergreen, large, outwardly spreading, inverted triangle. Vigorous. Numerous flowers per plant.

*Branching habit.*—Freely branching usually about four lateral branches develop after removal of terminal apex.

*Plant height, soil level to top of flowers.*—About 29 cm.

*Plant diameter, area of spead.*—About 52 cm.

*Lateral branch description.*—Length: About 23 cm. Diameter: About 5 mm. Color: Immature: 144B. Mature: 164A/166A. Texture: Pubescent.

Foliage description:

*Arrangement.*—Alternate, single.

*Length.*—About 4.5 cm.

*Width.*—About 2.3 cm.

*Shape.*—Elliptic.

*Apex.*—Mucronate.

*Base.*—Attenuate/cuneate.

*Margin.*—Entire.

*Texture.*—Leathery, pubescent on both surfaces.

*Color.*—Young foliage, upper surface: Darker than 147A. Young foliage, lower surface: Close to 147B. Mature foliage, upper surface: Darker than 147A. Mature foliage, lower surface: Close to 147B.

*Petiole.*—Length: About 5 mm. Diameter: About 2 mm. Color: 144A/144B.

Flower description:

*Natural flowering season.*—Spring after sufficient cool period.

*Time to flower* (*Forcing period*).—After about four to six weeks of cooling at 4 to 9° C. plants will typically require an additional three to five weeks to develop about 12 colored flower buds.

*Flower arrangement.*—Flowers arranged singly at terminals with usually five to ten flowers per apex. Flowers face upward and outward. Very freely flowering.

*Flower appearance.*—Large showy star-shaped single flowers. White and hot pink bi-colored petals. Flowers persistent.

*Flower diameter.*—About 9.5 cm.

*Postproduction longevity.*—Under interior conditions, plants maintain good flower substance for about four weeks.

*Flower bud* (*just starting to show petal color*).—Rate of opening: About three days depending on temperatures. Length: About 1.5 cm. Diameter: About 7.5 mm. Shape: Ovoid. Color: 144A.

*Petals.*—Appearance: Satiny. Texture: Smooth. Arrangement: Large single flowers. Corolla consists of five to seven fused petals. Sepals occasionally fused and petaloid. Shape: Spatulate with rounded apex. Margin: Entire with undulating edge which gives a ruffled appearance. Length: About 5.5 cm. Width: About 3.3 cm. Color: Fully opened, upper surface: Iridescent; center, 62B/62C/62D to white; margin, 57A/61B. Fully opened, lower surface: Iridescent; center, 62C/62D to white; margin, 57B/61C. Width of hot pink margin: About 1.7 cm. Throat: Faint, close to 63D speckles on upper petals.

*Sepals.*—Arrangement: Five sepals fused into a star-shaped calyx, occasionally petaloid. Texture: Slightly pubescent on lower surface and at margin. Shape: Variable, usually transitional structures with rounded or incised apices. Margin: Entire. Color, upper and lower surfaces: If petaloid, same as petals with variable green areas, 144A.

*Peduncles.*—Length: About 2 cm. Diameter: About 2 mm. Angle: Straight. Strength: Flexible, strong. Texture: Pubescent. Color: 144B, some reddish tones.

*Reproductive organs.*—Androeium: Stamen number: Usually about seven. Stamen length: About 4.2 cm. Stamen color: White. Anther shape: Oblong. Anther size: About 3 mm by 1.5 mm. Anther color: Golden brown. Amount of pollen: Moderate. Pollen color: Very light green to creamy white. Gynoecium: Stigma shape: Rounded. Stigma color: Close to 59B. Style length: About 4 cm. Style color: 57A. Ovary color: 144A, heavily whiskered.

Disease resistance: Good resistance to Cylindrocladium has been observed.

Seed production: Seed production has not been observed.

It is claimed:

1. A new and distinct Azalea plant named 'Parasol', as illustrated and described.

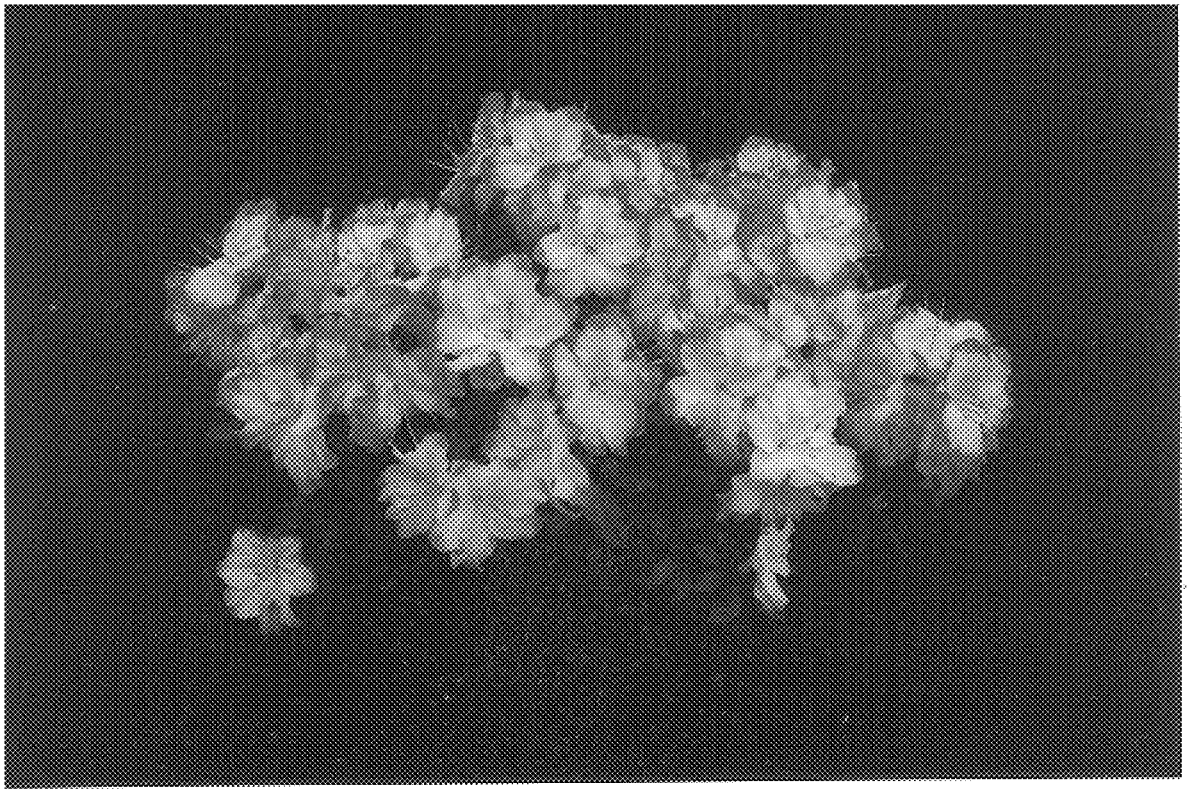
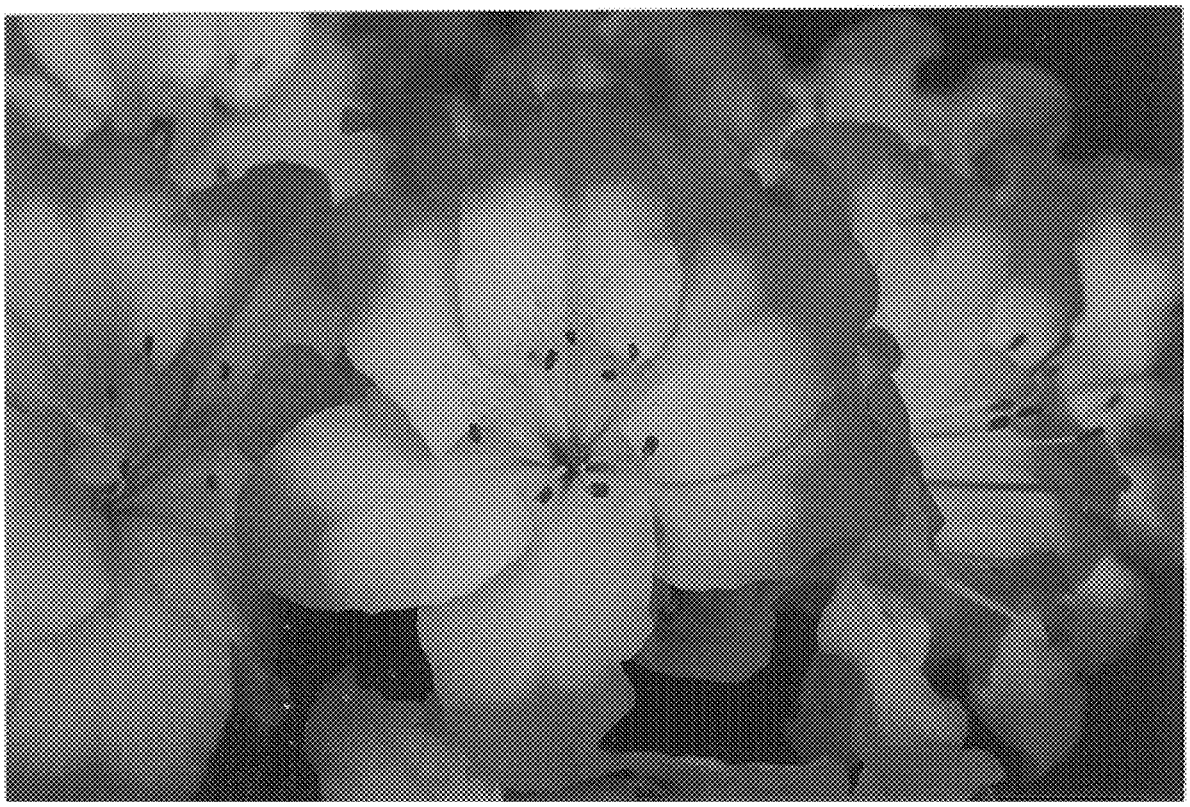

* * * * *